United States Patent [19]
Odo et al.

[11] 4,035,252

[45] July 12, 1977

[54] PROCESS FOR PRODUCING 2-AMINOMETHYL-1-ETHYLPYRROLIDINE

[75] Inventors: Keijiro Odo, Tokyo; Eiichi Ichikawa, Yokohama; Kazuharu Tamazawa, Shiraoka; Kozo Takahashi, Tokyo, all of Japan

[73] Assignee: Yamanouchi Pharmaceutical Co., Ltd., Tokyo, Japan

[21] Appl. No.: 712,389

[22] Filed: Aug. 6, 1976

[30] Foreign Application Priority Data

Aug. 11, 1975 Japan .............................. 50-97295

[51] Int. Cl.$^2$ ................. C25B 3/04; C07D 207/00
[52] U.S. Cl. ................................ 204/74; 204/59 R
[58] Field of Search ................... 204/74, 73 R, 59 R

[56] References Cited

U.S. PATENT DOCUMENTS

| 1,879,003 | 9/1932 | Alles | 204/74 X |
|---|---|---|---|
| 3,103,473 | 9/1963 | Juda | 204/77 |

FOREIGN PATENT DOCUMENTS

| 13,543 | 9/1900 | United Kingdom | 204/74 |

OTHER PUBLICATIONS

Zaporozhets et al., Sov. Electrochem (USA) vol. 8 pp. 1752–1755 (Dec. 1972).

Mosettig et al., J. Amer. Chem. Soc., vol. 60 pp. 2964, 2965 (Dec. 1938).

Primary Examiner—F.C. Edmundson
Attorney, Agent, or Firm—Burgess, Ryan and Wayne

[57] ABSTRACT

A process for producing 2-aminomethyl-1-ethylpyrrolidine by the electrolytic reduction of 1-ethyl-2-nitromethylenepyrrolidine.

6 Claims, No Drawings

PROCESS FOR PRODUCING 2-AMINOMETHYL-1-ETHYLPYRROLIDINE

DETAILED EXPLANATION OF THE INVENTION

The present invention relates to a novel and industrially advantagous process for producing 2-aminomethyl-1-ethylpyrrolidine. More particularly, this invention relates to a process for producing 2-aminomethyl-1-ethylpyrrolidine (II) by electrolytic reduction of 1-ethyl-2-nitromethylenepyrrolidine (I) under neutral to basic conditions using copper as the cathode.

2-Aminomethyl-1-ethylpyrrolidine (II) which is the aimed product of this invention is useful as intermediates for the syntheses of various medicaments.

As to method of producing 2-aminomethyl-1-ethylpyrrolidine (II) from 1-ethyl-2-nitromethylenepyrrolidine (I), there is known a method of reducing the starting material (I) with hydrogen in the presence of a catalytic hydrogenation metallic catalyst or with an acid and a metal, and in practically, the method wherein the catalytic reduction with hydrogen in the presence of Raney nickel catalyst is performed (U.S. Pat. No. 3,748,341 and British Pat. No. 1,374,818).

However, the method by catalytic reduction is insufficient for industrial practice since in the method a large amount of expensive Raney nickel catalyst is required and the yield is 65–81.7%.

As the result of various investigations under such a technical level, the inventors have discovered that by electrolytic reduction of the starting material (I) under neutral or basic condition using copper as the cathode, the highly-pure aimed product (II) can be obtained industrially advantageously at a high yield over 90%.

The electrolytic reduction in this invention is a cathodic reaction and the reaction scheme is shown as follows;

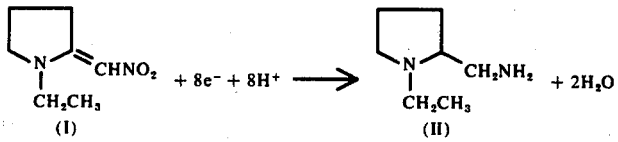

In the process of this invention, the highly-pure aimed product (II) can be obtained at yields over 90% as mentioned above and the materials consumed in the reaction are $8e^-$ and $8H^+$, that is, electrons and protons. Therefore, the process of this invention is industrially advantageous as compared with that of the known catalytic reduction using a large amount of expensive Raney nickel catalyst. Moreover, the process of this invention is also industrially advantageous in such points that it is unnecessary to remove from the reaction mixture unreacted reducing agent, catalyst or changed materials thereof and the reaction of this invention does not require severe conditions such as high temperature, high pressure, etc..

In addition, it is known that a 2-aminoethyl compound belonging to a saturated alkylamine as well as the aimed product (II) is produced by electrolytic reduction of a β-nitrostyrene belonging to an α-nitroolefin as well as the starting material (I) under an acid condition using mercury or lead as the cathode (Kirk-Othmer, "Encyclopedia of Chemical Technology", Vol. 5, 664 (1960). However, it has been unexpectedly found that, in the electrolytic reduction of this invention, the desired result is not provided when the electrolytic reduction is carried out under an acid condition above mentioned, but the desired result is provided when the electrolytic reduction is carried out only under neutral to basic condition using copper as the cathode.

Now, the results obtained by electrolytic reduction of the starting material (I), 1-ethyl-2-nitromethylenepyrrolidine under various conditions are shown below.

Experimental procedure:

The experiment was carried out using an H-type electrolytic apparatus having a sintered-glass diaphragm or a B-type electrolytic apparatus having a porous unglazed cylinder at the center as a diaphragm. A cathode and a catholyte solution were placed in the cathode chamber of the apparatus and a platinum disc (30 mm. diameter) as an anode and an anolyte solution were placed in the anode chamber. Then, after pre-electrolysis for 10 minutes, the starting material (I), 1-ethyl-2-nitromethylenepyrrolidine was added to the cathode chamber and a controlled current of 0.8–1.0 ampere was electrified until a theoretical or slightly excessive quantity of electricity. Thereafter, the formed amount of the aimed product (II), 2-aminomethyl-1-ethylpyrrolidine was determined from the thin layer chromatogram of the reaction product. The result is shown in Table 1.

Table 1

| Run | Cathode | (mm²) | Electrolyte solution | (ml) | Amount of starting material (I) (g) | Current (ampere) | Electrolytic apparatus | Amount of aimed product (II) |
|---|---|---|---|---|---|---|---|---|
| 1 | Pb (flatt) | (30×40) | A* | (80) | 1.56 | 1.0 | H-type | Trace |
| 2 | Pb (sponge) | (″) | ″ | (″) | ″ | ″ | ″ | ″ |
| 3 | Hg | (12 cm²) | ″ | (″) | ″ | ″ | ″ | None |
| 4 | Cu | (40×180) | ″ | (″) | ″ | ″ | B-Type | ″ |
| 5 | Pb (flatt) | (30×40) | B-1* | (80) | ″ | ″ | H-Type | ″ |
| 6 | Pb (sponge) | (″) | ″ | (″) | ″ | ″ | ″ | ″ |
| 7 | Zn | (″) | ″ | (50) | 0.8 | ″ | ″ | ″ |
| 8 | Ni | (″) | ″ | (″) | ″ | ″ | ″ | ″ |
| 9 | Al | (″) | ″ | (″) | ″ | ″ | ″ | ″ |
| 10 | 18-8 Stainless steel | (25×40) | ″ | (″) | ″ | 0.8 | ″ | ″ |
| 11 | Graphite | (″) | ″ | (″) | ″ | ″ | ″ | ″ |
| 12 | Sn | (″) | ″ | (″) | ″ | ″ | ″ | ″ |
| 13 | Cd | (40×180) | ″ | (100) | 1.56 | 1.0 | B-Type | ″ |
| 14 | Cu | (30×40) | ″ | (50) | 0.8 | ″ | H-Type | Large quantity |

Table 1-continued

| Run | Cathode | (mm²) | Electrolyte solution (ml) | Amount of starting material (I) (g) | Current (ampere) | Electrolytic apparatus | Amount of aimed product (II) |
|---|---|---|---|---|---|---|---|
| 15 | Cu | (40×180) | B-2* (100) | 1.56 | " | B-Type | " |

In addition, in the above table, the marks (*) of electrolyte solution are as follows:

| Mark | Catholyte solution | Anolyte solution |
|---|---|---|
| A | 20% $H_2SO_4$-MeOH (1:1 v/v) | 20% $H_2SO_4$ |
| B-1 | 2% $NH_4OH$-MeOH (7:3 v/v) saturated with $(NH_4)_2SO_4$ | Saturated aqueous $(NH_4)_2SO_4$ solution |
| B-2 | 2N $Na_2CO_3$-MeOH (7:3 v/v) passing $CO_2$ | Saturated aqueous $Na_2CO_3$ solution |

As clear from the result shown in the table, in Run No. 1-4 wherein acid electrolyte solutions were used, the aimed product (II) was scarecely formed and in Run No. 5-15 wherein basic electrolyte solutions were used, the aimed product (II) was obtained in only Run No. 14 and 15 wherein copper was used as the cathode.

The process of this invention is carried out by electrolytic reduction of the starting material (I) under neutral to basic condition using copper as the cathode. Practically, since the electrolytic reduction of this invention is a cathodic reaction, the reduction is carried out by adding the starting material (I) to neutral to basic aqueous electrolyte solution in a cathode chamber of an electrolytic apparatus and electrifying a theoretical or excessive quantity of electricity. In this case, it is preferred that an organic solvent be added to the cathode chamber since the starting material (I) is insoluble in water and the starting material (I) may be added to the cathode chamber as an organic solvent solution of it. The organic solvent used for the purpose is an inert organic solvent which is miscible with water and dissolves the starting material (I). Example of the proper solvent is an alcohol such as methanol, ethanol, etc.

The electrolytic reduction of this invention is advantageously practiced using an electrolytic apparatus separated into a cathode chamber and an anode chamber by a porous diaphragm such as a porous unglazed diaphragm (porous unglazed cylinder, etc.,), a porous glass plate (sintered-glass diaphragm, etc.,), an ion-exchange membrane, membrane filter, etc.

The cathode material in this invention is copper and the copper may include copper alloy such as brass (copper-zinc alloy). There is no particular restriction about the shape of the cathode. For example, a plate, a net, a perforated plate, etc., may be used. Also, any insoluble electrodes can be used as the anode material in this invention. For example, platinum, palladium, etc., can be used and there is no particular restriction about the shape of the anode as in the case of the cathode.

The aqueous electrolyte solution used in this invention is neutral to basic, preferably neutral to weak basic (pH of about 7 to about 11) aqueous electrolyte solution. Examples of such an aqueous electrolyte solution is aqueous ammonium sulfate solution, aqueous solution of ammonium sulfate and ammonium hydroxide, aqueous sodium acetate solution, aqueous sodium carbonate solution, and aqueous sodium hydrogen-carbonate solution. In this case, it is preferred to maintain the property of the aqueous electrolyte solution constant throughout the electrolytic reduction and thus when, for example, aqueous sodium hydrogencarbonate or aqueous sodium carbonate solution is used, it is preferred to carry out the electrolytic reduction while passing carbon dioxide through the electrolyte solution.

There is no particular restriction about the reaction temperature in the electrolytic reduction of this invention and for example, the electrolytic reduction is performed at 0°-100° C. but very high temperature must not be employed for preventing the occurence of the decomposition of the starting material (I) and the aimed product (II) formed as well as the occurence of undesiable side reactions. The electrolytic reduction of this invention is usually carried out at room temperature.

The reaction times depend upon the concentration of the starting material (I), the kind and the concentration of the electrolyte, the current, etc., but the end point of the reaction is generally the point when the starting material (I) is consumed. For example, the end point of the reaction, that is, the consumed point of the starting material (I) may be found by checking the disappearance of the starting material (I) by thin layer chromatography with the passage of time.

The electrolysis is carried out by electrifying a theoretical or excessive quantity of electricity through the electrolyte solution. In addetion, it is preferred to carry out a so-called pre-electrolysis prior the reaction for preventing the occurence of unexpected troubles.

The aimed product (II) thus obtained can be recovered at a high purity by purifying the reaction product by an ordinary chemical operation such as distillation under reduced pressure, etc.

EXAMPLE 1

A 200 ml. glass beaker having inserted therein a porous unglazed cylinder (40 mm. diameter × 140 mm. length) was used as an electrolytic apparatus and a copper plate (40 × 180 mm²) as the cathode and a platinum disc (30 mm. diameter) as the anode were used. In the anode chamber (the porous unglazed cylinder) was added 50 ml. of a saturated aqueous sodium carbonate solution and in the cathode chamber (the glass berker) were added 70 ml. of a 2 N aqueous sodium carbonate solution and 30 ml. of methanol. Then, after carrying out pre-electrolysis for several minutes while passing carbon dioxide through the catholyte solution, 1.56 g. of powder of 1-ethyl-2-nitromethylenepyrrolidine was added to the cathode chamber and current of 1 ampere was electrified for 2.5 hours with stirring at 20°-25° C while passing carbon dioxide through the catholyte solution to carry out electrolysis. After the electrolysis was over, the catholyte solution was acidified with diluted hydrochloric acid and then methanol was distilled off under reduced pressure. The residue formed was made strongly basic with a diluted aqueous sodium hydroxide solution, and then the resulting solution was extracted with ether. The ether extract thus formed was dried over anhydrous magnesium sulfate, ether was distilled off, and then the residue formed was subjected to distillation under reduced pressure to provide 1.22 g. of oily 2-aminomethyl-1-ethylpyrrolidine with a yield of 95%. The product could be distilled at a boiling point of 58°-60° C. (16 mm Hg).

The infrared absorption spectrum of the product coincided with that of the standard product.

EXAMPLE 2

An H-type glass apparatus separated into an anode chamber and a cathode chamber at the middle by a sintered-glass diaphragm was used as the electrolytic apparatus and a copper plate (30 × 40 mm$^2$) as the cathode and a platinum disc (30 mm.diameter) as the anode were used. In the anode chamber were added 40 ml. of a saturated aqueous ammonium sulfate solution and 10 ml. of an aqueous 28% ammonium hydroxide solution and in the cathode chamber was added 50 ml. of an aqueous 30% methanol solution saturated with ammonium sulfate. Then, after carrying out pre-electrolysis for several minutes, 0.78 g. of the powder of 1-ethyl-2-nitromethylenepyrrolidine was added to the cathode chamber and the current of 1 ampere was electrified for 2 hours with stirring at 20°-25° C. to carry out the electrolysis. Then, by treating the product as in Example 1, 0.59 g. of oily 2-aminomethyl-1-ethyl-pyrrolidine was obtained with a yield of 90%.

The infrared absorption spectrum of the product coincided with that of the standard product.

EXAMPLE 3

A 200 ml. glass beaker having inserted therein a porous unglazed cylinder (40 mm. diameter × 140 mm. length) was used as the electrolytic apparatus and a copper plate (40 × 180 mm$^2$) as the cathode and a palladium plate (30 × 40 mm$^2$) as the anode were used. In the anode chamber (the porous unglazed cylinder) was added 50 ml. of a saturated aqueous sodium carbonate solution and in the cathode chamber (the glass beaker) were added 70 ml. of a 2 N aqueous sodium carbonate solution and 30 ml. of methanol. Then, after carrying out pre-electrolysis for several minutes while passing carbon dioxide through the catholyte solution, 1.56 g. of the powder of 1-ethyl-2-nitromethylenepyrrolidine was added to the cathode chamber and current of 1 ampere was electrified for 2.5 hours with stirring at 20°-23° C. while passing carbon dioxide through the catholyte solution to carry out the electrolysis. Then, by treating the product as in Example 1, 1.22 g. of oily 2-aminomethyl-1-ethylpyrrolidine was obtained with a yield of 95%.

The infrared absorption of the product coincided with that of the standard product.

EXAMPLE 4

A 200 ml. glass beaker having inserted therein a porous unglazed cylinder (40 mm. diameter × 140 mm. length) was used as the electrolytic apparatus and a copper plate (40 × 180 mm$^2$) as the cathode and hastelloy plate (30 × 40 mm$^2$) as the anode were used. In the anode (the porous unglazed cylinder) was added 50 ml. of a saturated aqueous sodium carbonate solution and in the cathode (the glass beaker) were added 70 ml. of a 2 N aqueous sodium carbonate solution and 30 ml. of methanol. Then, after carrying out pre-electrolysis for several minutes while passing carbon dioxide through the catholyte solution, 1.56 g. of the powder of 1-ethyl-2-nitromethylenepyrrolidine was added to the cathode chamber and the current of 1 ampere was electrified for 2.5 hours with stirring at 20°-23° C. while passing carbon dioxide through the catholyte solution to carry out electrolysis. After the electrolysis was over, the catholyte solution was acidified with diluted sulfuric acid and then methanol was distilled off under reduced pressure. The residue formed was made strongly basic with a diluted aqueous sodium hydroxide solution, and then the resulting solution was extracted with ether. The ether extract was then dried over anhydrous potassium carbonate, ether was distilled off, and the residue formed was subjected to distillation under reduced pressure to provide 1.22 g. of oily 2-aminomethyl-1-ethylpyrrolidine with a yield of 95%. The product could be distilled at a boiling point of 58°-60° C. (16 mm Hg).

The infrared absorption spectrum of the product coincided with that of the standard product.

EXAMPLE 5

An H-type glass apparatus separated into an anode chamber and a cathode chamber at the middle by a sintered-glass diaphragm was used as the electrolytic apparatus and a copper plate (30 × 40 mm$^2$) as the cathode and a lead plate (30 × 40 mm$^2$) as the anode were used. In the anode chamber were added 40 ml. of a saturated aqueous ammonium sulfate solution and 10 ml. of an aqueous 28% ammonium hydroxide solution and in the cathode chamber was added 50 ml. of an aqueous 30 % methanol solution saturated with ammonium sulfate. Then, after carrying out pre-electrolysis for several minutes, 0.78 g. of the powder of 1-ethyl-2-nitromethylenepyrrolidine was added to the cathode chamber and the current of 1 ampere was passed for 2 hours with stirring at 20°-23° C. Then, by treating the product as in Example 1, 0.59 g. of oily 2-aminomethyl-1-ethylpyrrolidine was obtained with a yield of 90%.

The infrared absorption spectrum of the product coincided with that of the standard product.

What is claimed is:

1. A process for producing 2-aminomethyl-1-ethylpyrrolidine which comprises electrolytic reduction of 1-ethyl-2-nitromethylenepyrrolidine under neutral to basic condition using copper as the cathode.

2. The process as claimed in claim 1 wherein said neutral to basic condition is neutral to weak basic.

3. The process as claimed in claim 1 wherein the electrolytic reduction is carried out in an aqueous electrolyte solution containing an organic solvent.

4. The process as claimed in claim 3 wherein said organic solvent is methanol.

5. The process as claimed in claim 3 wherein the electrolyte solution containing an organic solvent is a weak basic aqueous solution containing methanol.

6. The process as claimed in claim 1 wherein said electrolytic reduction is carried out in an aqueous sodium carbonate solution containing methanol while passing carbon dioxide through the catholyte solution.

* * * * *